(12) United States Patent
Naftal

(10) Patent No.: US 8,708,423 B2
(45) Date of Patent: Apr. 29, 2014

(54) CUSTOMIZABLE MODULAR BRUSH SYSTEM AND METHOD THEREOF

(71) Applicant: Keystone Plastics, Inc., South Plainsfield, NJ (US)

(72) Inventor: Brian Naftal, South Plainsfield, NJ (US)

(*) Notice: Subject to any disclaimer, the term of this patent is extended or adjusted under 35 U.S.C. 154(b) by 0 days.

(21) Appl. No.: 13/951,089

(22) Filed: Jul. 25, 2013

(65) Prior Publication Data

US 2013/0305473 A1    Nov. 21, 2013

Related U.S. Application Data

(62) Division of application No. 12/799,544, filed on Apr. 27, 2010, now Pat. No. 8,495,786.

(51) Int. Cl.
*A46B 7/10*    (2006.01)

(52) U.S. Cl.
USPC ................ 300/21; 15/179; 15/176.6; 15/202; 15/183

(58) Field of Classification Search
USPC .......... 15/176.6, 176.1, 176.3, 179, 180, 183, 15/194, 201, 202; 300/21
See application file for complete search history.

(56) References Cited

U.S. PATENT DOCUMENTS 6,536,067 B1 *  3/2003  Truan et al. ................. 15/78
6,817,055 B1 * 11/2004  Ekholm ..................... 15/183

* cited by examiner

*Primary Examiner* — Shay Karls
(74) *Attorney, Agent, or Firm* — Howard C. Miskin, Esq.; Gloria Tsui-Yip, Esq.

(57) ABSTRACT

A system and method that utilizes modular components to form a customizable brush for different applications with ease and at a low cost. The system and method utilizes three main components: a base, a plurality of rails, and a plurality of strip brush elements. The plurality of rails is fastened to the base and the plurality of rails holds the strip brush elements to the base to form a brush. All three components may be made of a thermoplastic or thermoset, non-metallic material which can be either rigid or flexible to allow the resulting brush to be easily recyclable.

21 Claims, 21 Drawing Sheets

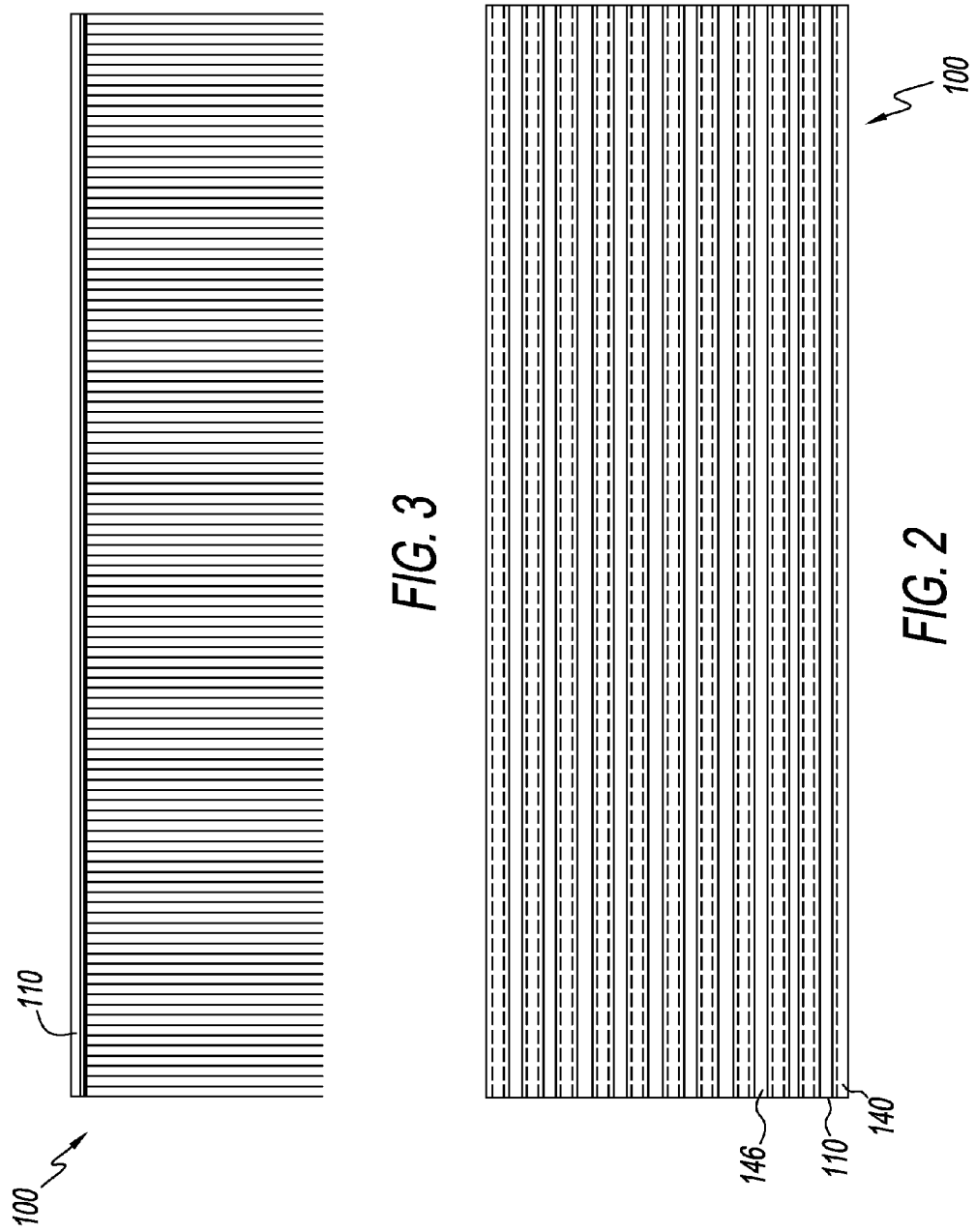

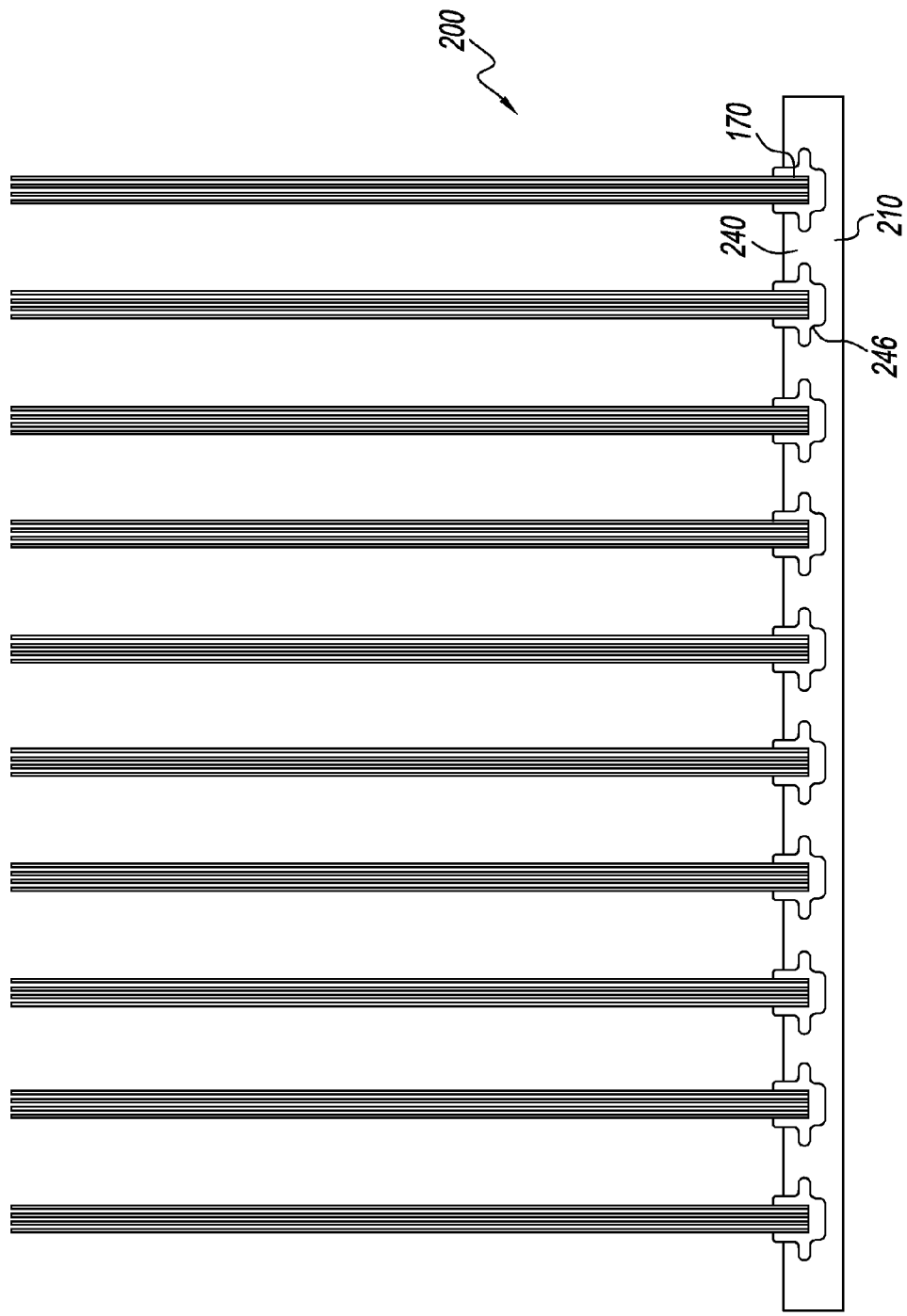

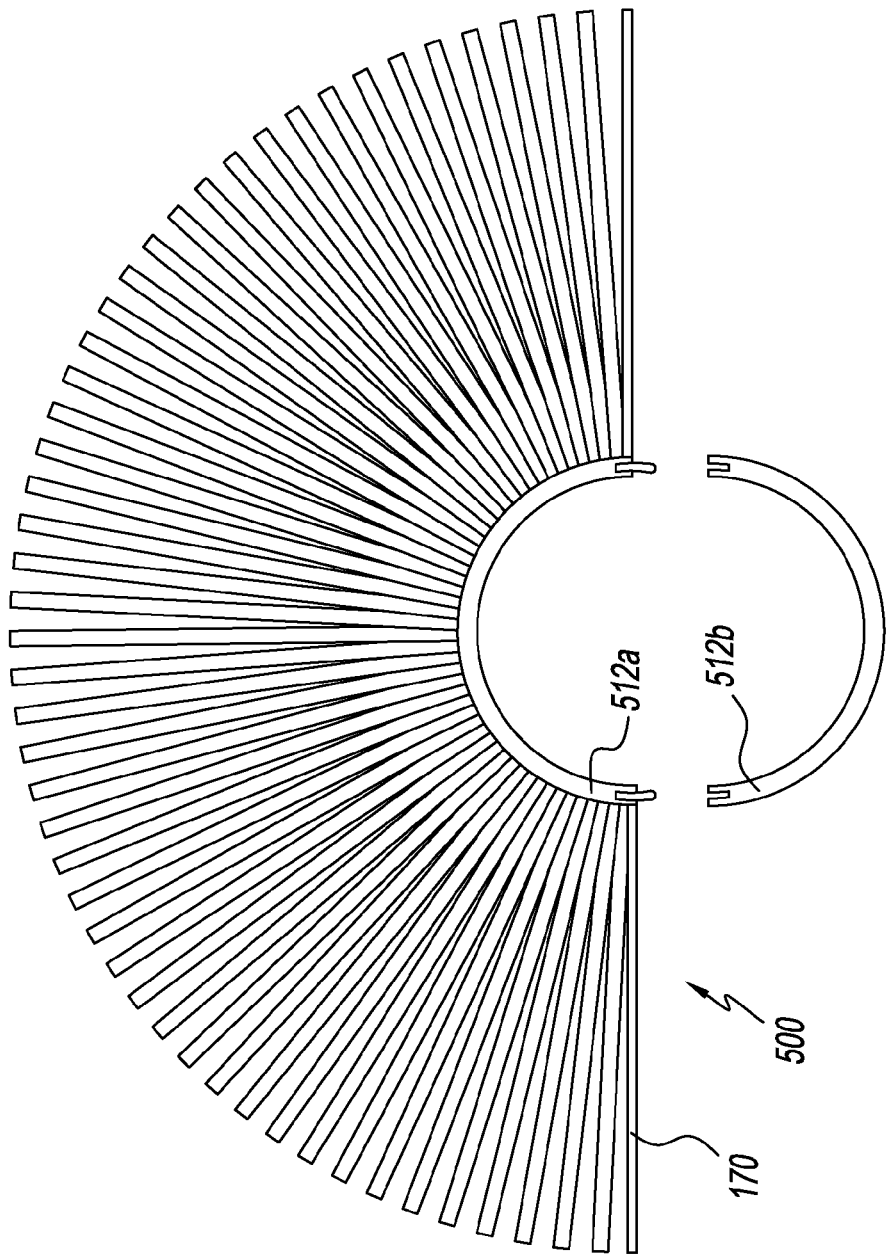

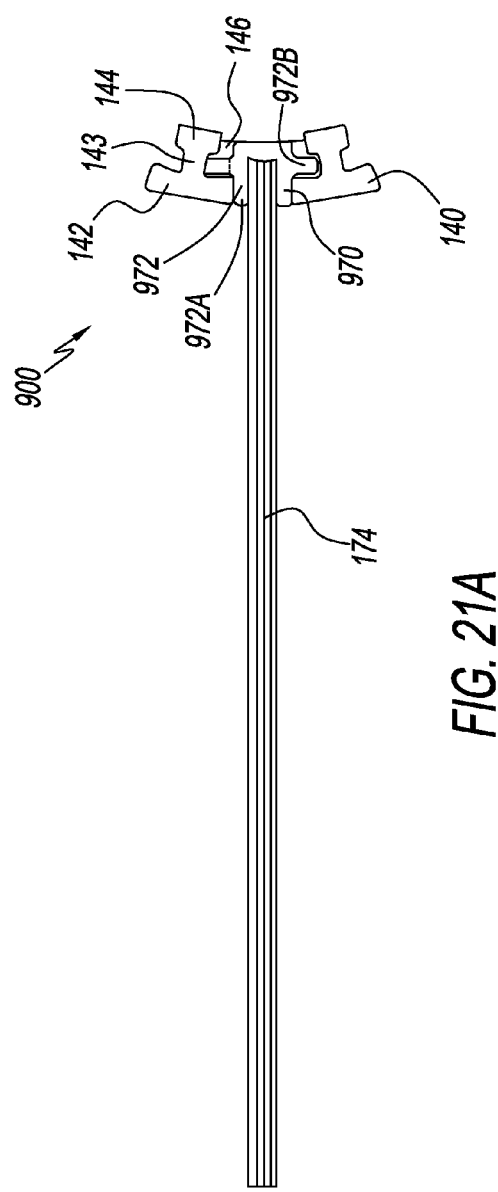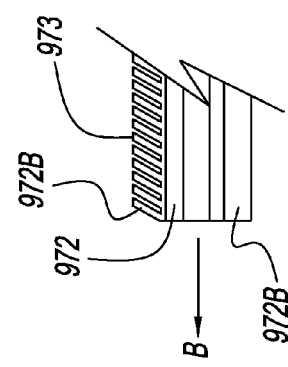
FIG. 21A
FIG. 21B

US 8,708,423 B2

CUSTOMIZABLE MODULAR BRUSH SYSTEM AND METHOD THEREOF

CROSS-REFERENCE TO RELATED APPLICATION

This is a divisional application of pending application Ser. No. 12/799,544 filed on Apr. 27, 2010, which is hereby incorporated by reference.

FIELD OF THE INVENTION

The invention relates to a customizable modular brush system and method thereof. In particular, a system that utilizes modular components to provide a customizable brush for different applications with ease and at a low cost.

BACKGROUND OF THE INVENTION

Different types of brushes are utilized in different industries and for different applications. Commercial brushes, such as those for use in connection with street sweepers, car washes, in-plant sweepers, airports, etc., are highly customized for its specific application. Typically, due to the varied developments over the years of commercial brushes, brushes used in one industry cannot easily be adapted for use in another industry. Different manufacturers use different machinery to produce the brushes. Therefore, purchaser of a brush for a particular industry or application has limited sources. And since a manufacturer is unable to provide brushes to different industries, it cannot readily benefit from the reduced cost savings resulting from mass production.

Even within an industry, such as street sweeping, different brushes are used. A street sweeper typically has a reusable cylindrical core with replaceable radiating brush elements attached to the vehicle and a replaceable gutter broom with downward extending brush elements on each side of the vehicle. While the core with brush elements and gutter broom are normally produced by the same manufacturer, the processes for their manufacturing are very different and require separate sets of machinery to produce.

Different industries also use a reusable cylindrical core similar to those used in street sweepers. For example, airport brush cassettes, car washes, etc. Currently, such cores are made out of metal. On the outer surface of the core, along the longitudinal axis, is a plurality of U-shape channels for receiving strips of bristles that are made out of metal or plastics. The mixed use of a metal core with either metal or plastic bristles does not allow such brush to be easily recyclable. There are two typical prior art methods of producing these U-shape channels on the core.

One prior art method is by extrusion, wherein the combined U-shape channels and core are extruded. See U.S. Pat. No. 6,817,055 to Hans Ekholm. There are many disadvantages and limitations to this prior art process: (1) dies used for the extrusion process is limited in size so that only certain maximum diameters can be produced; (2) extruded sections are extremely heavy since the material is thick and is impossible to reduce the mass by inserting cavities; (3) extremely expensive tooling costs, and in most cases, restricted to shapes and sizes for a particular industry or market; (4) extruded metal tends to cure and bend while cooling, requiring the need to rework for dynamic balancing for high speed usage; (5) extruded U-shape channels must align with the axial length of the core; and (6) difficult, if not impossible, to provide different patterns (such as helix, or non-linear) on the core.

Another prior art method is by welding a U-shape channel onto a core. Each U-shape channel is formed by roll forming a flat metal sheet, then pinched. There are many disadvantages and limitations to this prior art process: (1) dies used for the roll forming of the U-shape channel is limited in size so that only certain maximum diameters can be produced; (2) each U-shape channel has a maximum width before it will not make sufficient contact with the core; (3) extremely expensive tooling costs, and in most cases, restricted to shapes and sizes for a particular industry or market; (4) if non-corrosive material is needed, expensive and difficult to work with when welding; (5) requires the use of a large and expensive spot welding machine to weld the U-shape channels to the core; (6) axial length of the core is limited to the size of the spot welding machine; (7) skilled and time intensive labor required to weld the seams of the U-shape channels every few inches across the entire length of the core to prevent the U-shape channels from pulling off at the seam; (8) U-shape channels can only be mounted along the axial length of the core; and (9) difficult, if not impossible, to provide different patterns (such as helix or non-linear) on the core.

Currently the most common process that allows different patterns on brushes is a staple set machine that staples bristles directly to a non-metallic core. There are many disadvantages and limitations to a staple set brush: (1) the core cannot be efficiently reused since the metal staples must first be removed; (2) core must be of sufficient thickness to support the stapled bristles; (3) the use of a thick core is costly; and (4) the use of a thick core is heavy, difficult to manipulate and increases shipping costs.

Therefore, there is a need for an improved brush system that is modular to allow production of customizable brush that can be used in different industries and applications with ease, at a low cost and also easily recyclable.

SUMMARY OF THE INVENTION

The brush system of the present invention utilizes modular components to produce a customizable brush with ease and at a low cost. Further, the brush system of the present invention may be entirely made of plastic material(s) to allow the resulting brush to be easily recyclable. The method of the brush system of the present invention can produce brushes for infinite brush applications. Further, the method of the brush system of the present invention can produce brushes for all existing industries and applications.

The brush system utilizes three (3) main components: a base, a plurality of rails, and a plurality of strip brush elements. The plurality of rails is attached to the base and the plurality of rails holds the strip brush elements to the base to form a brush. All three components may be made of a thermoplastic or thermoset, non-metallic material which can be either rigid or flexible.

The base can be of various shapes, such as tubular, prism, flat, arcuate, etc., and have various cross-sections, such as rectangular, circular, etc. Optionally, a plurality of grooves is provided on the base to receive the plurality of rails to provide increased contact surfaces between the base and the rails. The grooves may take on various forms, such as linear, curved or any other desirable configuration or pattern, and may have various cross-sectional shapes. The density and pattern of the grooves can be easily formed depending on the intended application of the resulting brush.

Each rail is elongated and has a cross section that has a generally wider upper profile and a generally narrower lower profile such as T-shape, U-shape with overhanging ends, upside down Ω-shape, etc. The lower portion of the rail is fastened onto the surface of the base or, optionally into the grooves, by adhesive, epoxy, mechanical fastening, chemical fastening, sonic fastening or fusion fastening. The rails can be configured and fastened to the base with various density and pattern or can be configured to take on the configuration or pattern of the grooves. Adjacent rails form a channel having a cross-section with a narrower upper profile and a wider lower profile for receiving and securing a strip brush element onto the base. The width of the channels can vary depending on the distance between adjacent rails. Optionally, the base and rails are formed integrally by milling the channels into a thicker base.

Each strip brush element has a coupling end and at least one brush element extending therefrom. The brush element can be in the form of bristles, tufts of bristles, baffle strip, stripping, etc. and made of metal, felt, thermoplastic, thermoset, micro fiber, or other flexible material, etc. The cross section of the coupling end has a wider profile than the brush element profile such that the strip brush element is received and secured in the channel formed between adjacent rails. The coupling end of the strip brush element can have different widths for secured receipt in the channels. A narrower or flexible coupling end provides the flexibility to conform to curved, or other patterned, channels. After sliding the strip brush element into and between the channels, a holder can be mounted onto the base or the rails to prevent the strip brush element from sliding out of the rails.

The use of thermoplastic or thermoset material in the brush system of the present invention allows efficient, quick and easy customization of each modular component at a low cost, with the resulting brush being easily recyclable, and even possibly bio-degradable. The density and pattern of the resulting brush can be customized by manipulating the width, density and pattern of the rails and strip brush elements. Different types of brushes for use in different industries and different applications can be produced with different sizes and shapes bases. There is no limitation on the size or shape of the resulting brush. There is minimal tooling cost and there is no need to use highly skilled welding professionals in connection with the brush system of the present invention. A customized brush of the present invention can easily be produced as by a mass production. Small quantities of unique brushes can be easily fabricated with simple fabrication equipments and minimally skilled laborer.

BRIEF DESCRIPTION OF THE DRAWINGS

Preferred embodiments of the present invention have been chosen for purposes of illustration and description and are shown in the accompanying drawings forming a part of the specification wherein:

FIG. 2 is a top view of the base and rails of FIG. 1.

FIG. 3 is a front view of the brush of FIG. 1.

FIG. 5 is a side view of another embodiment of the brush of the present invention similar to FIG. 1 but with integral rails.

FIG. 14 is a side view of FIG. 13.

FIG. 21A-21B show the partial side and top views of another embodiment of the brush of the present invention similar to FIG. 10 but the coupling end of the strip brush element having a feather board side.

DETAILED DESCRIPTION OF THE PREFERRED EMBODIMENTS

Figure 1:
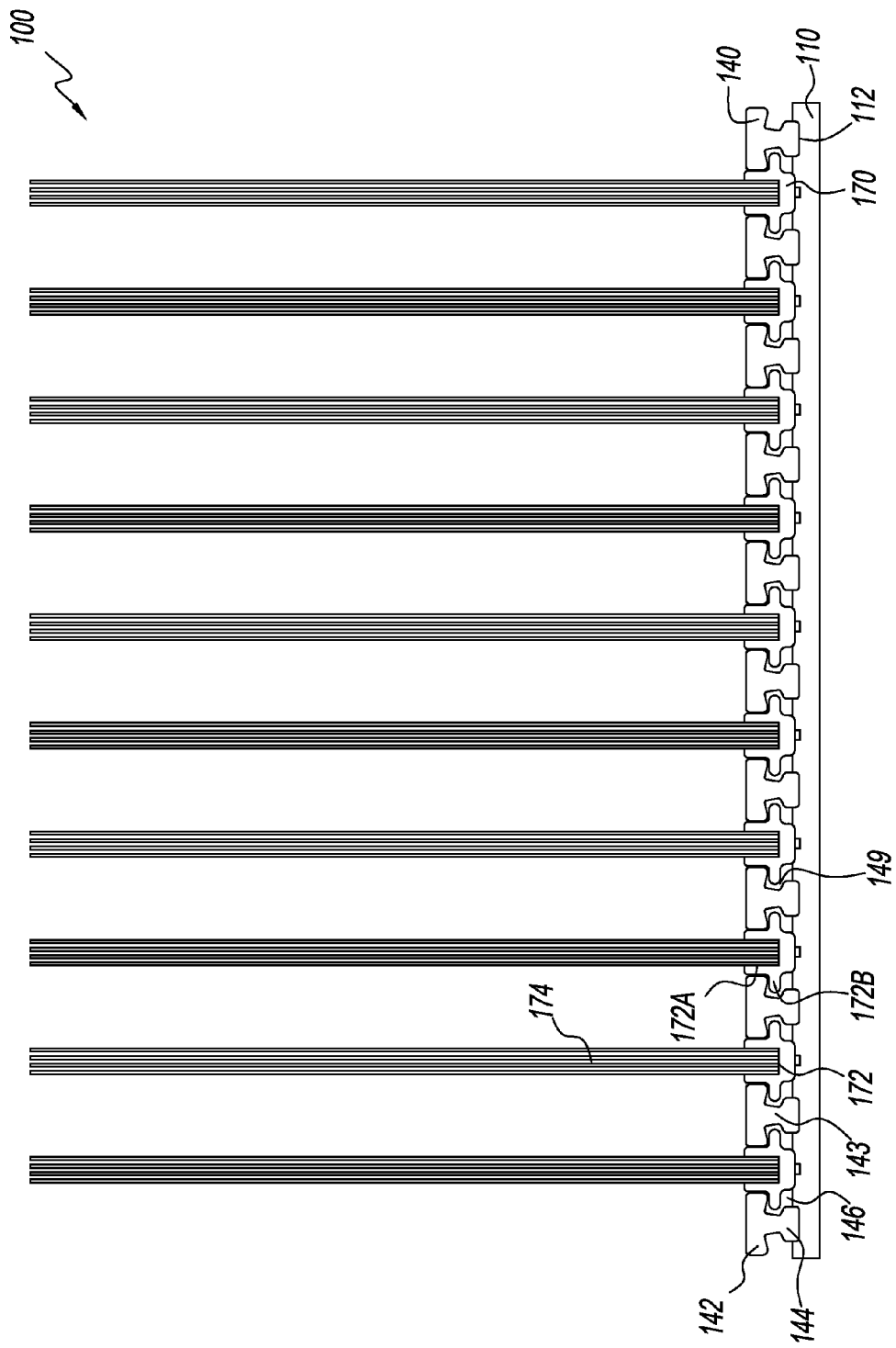
FIG. 1 is a side view of the brush of the present invention having a planar rectangular base with longitudinal rails.

With reference to the drawings, wherein the same reference number indicates the same element throughout, there is shown in FIGS. 1-3 a brush 100 of the present invention. The brush 100 comprises a base 110, a plurality of rails 140 and a plurality of strip brush elements 170, all of which may be made of a thermoplastic or thermoset material. Each of these components, base 110, rail 140 and strip brush element 170, may be extruded, molded, or otherwise produced by methods known to one skilled in the art.

As shown in FIGS. 1-3, base 110 has a planar rectangular shape with a plurality of spaced apart and longitudinal grooves 112 on its surface. Grooves 112 are formed on the base 110 by cutting, carving, grounding, etching or milling. The density of the grooves 112 can be customized to the specific application or use. A plurality of elongated rails 140 are fastened, spaced apart and longitudinally, in the grooves 112 of the base 100 by means known to one skilled in the art, but possibly without the use of metal parts.

The surfaces of the grooves 112 can be roughed up to further improve the contact and fastening with the rails 140. While grooves 112 is shown in FIGS. 1-3 to be linear and having a rectangular cross section, the grooves 112 may be curved or any other desirable configuration or pattern and may have various cross-sectional shapes such as those grooves 112a-112c shown in FIGS. 4A-C. The grooves 112a-112c having various cross-sectional shapes shown in FIGS. 4A-4C further improve the contact and fastening with the rails 140.

Figure 4A:
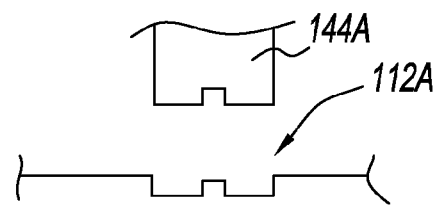
FIGS. 4A-4C illustrate cross-sections of different grooves.
Figure 4B:
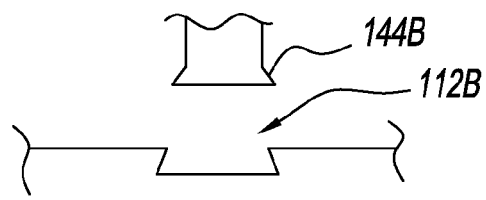
Figure 4C:
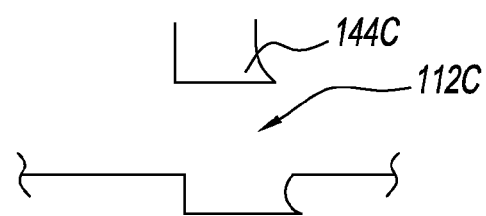

As shown in FIG. 1, each rail 140 is elongated and has a cross section that is generally T-shape. Rails with other cross-sectional shapes, such as U-shape with overhanging ends, upside down Ω-shape, having an upper portion 142 with a wider profile than a lower portion 144 with a narrower profile can also be used. The T-shape rail 140 as shown in FIG. 1 has a mid portion 143 with a tapered profile, which is optional. The lower portion 144 is shown to correspond and fit snuggly in the groove 112. For grooves 112a-112c as shown in FIGS. 4A-4C, the lower portions 144a-144c are correspondingly shaped to fit within the grooves. For groove 112b, the lower portion 144b may be longitudinally slid into it for fastening. For groove 112c, the lower portion 144c may be snapped into it for fastening. The lower portion 144 may also be tapered, or notched (not shown) to provide additional spacing between the rail 144 and the groove 112 to allow adhesive to set in between for improved fastening. Further, the lower portion 144 may have a latch extension (not shown) that cooperates with an opening on the base 100 for additional support and secured attachment. While the grooves 112 are shown on the base 110, the rails 140 can also be fastened directly onto the surface of the base 110. Adjacent rails 140 form a channel 146 therebetween with an upper space 148 having a narrower profile and a lower space 150 having a wider profile. Optionally, the channel 146 has a mid space 149 having the widest profile. The width of the channel 146 can vary depending on the distance between adjacent rails 140, which can be easily customizable.

As shown in FIG. 1, each strip brush element 170 is elongated with a coupling end 172 with a brush element 174 extending therefrom, generally known to one skilled in the art. A prior art strip brush element 170 that may be modified and used in connection with the present invention is disclosed in U.S. Pat. No. 5,819,357 to Frances Gould (which is inserted into a metal drum). Other prior art strip brush element may also be adapted to be used with the present invention. As shown in FIGS. 1 and 3, the brush element 174 is shown to be a continuous row of bristles. The brush element 174 can be made from a variety of materials generally known to one skilled in the art. The cross section of the coupling end 172 corresponds to the cross sectional profile of the channel 146 such that the coupling end 172 can slidably and frictionally fit in the channel 146 to be held in position by adjacent rails 140. As shown in FIG. 1, the cross sectional profile of the coupling end 172 has a narrowest upper section 172A and a widest mid section 172B to be correspondingly secured by the upper portion 142, and mid and lower portions 143 and 144, of the rail 140, respectively. The use of thermoplastic or thermoset provides a low coefficient of friction for the base 110, rails 140 and strip brush elements 170 such that the strip brush elements 170 can fit tightly (with little tolerance) in the channels 146 to reduce rocking when the brush 100 is being used. The prior art brush's use of different materials (such as metal and plastic) for different portions of the brush disadvantageously allows more rocking, which in the long run can damage both the brush and the driving mechanism. The coupling end 172 can have different widths for secured receipt in the channels 146. While FIG. 1 shows a strip brush element 170 in each channel 146, further customization can be accomplished by selectively positioning strip brush element 170 in only certain, but not all, channels 146. Similarly, while FIG. 1 shows a strip brush element 170 extending across the full length of the channel 146, further customization can be accomplished by using shorter strip brush element 170 discretely positioned along the channels 146. Brush 100 may have brush elements 174 made out of the same or different materials, depending on the application. The strip brush elements 174 are prevented from sliding out of the channels 146 by providing a holder (not shown) that can be attached to the base 110 or the rails 140, whether on the planar surface or on the sides of the base 110.

Brush 100 can be customized by the selective positioning of the grooves 112 and/or rails 140 and the spaces between adjacent rails 140. The widths of the rails 140 and the coupling ends 172 of the strip brush elements 170 can vary for further customization. Brush elements 174 made of different materials can be selectively inserted in the channels 146 for additional customization.

The method of producing a customizable brush of the present invention, such as brush 100, requires a base 110 of any shape or size, a plurality of elongated rails 140 of any width and length, and a plurality of strip brush elements 170 of any width and length. A plurality of grooves 112, of any desirable pattern, may optionally be cut on the surface of the base 110. The rails 140 are fastened either directly on the surface of the base 100 or in the grooves 112. The rails 140 are fastened to the base to produce any desirable pattern. A strip brush element 170 is then inserted between adjacent rails 140 to form a customized brush.

FIG. 5 shows a brush 200 similar to brush 100 of FIGS. 1-3. The top and front views of the brush 200 are the same as FIGS. 2-3. The difference between the brush 200 and brush 100 is that the rails 240 are formed integrally with the base 210. The integral rails 240, and the corresponding channels 246, are formed by cutting, carving, grounding, etching or milling into a planar rectangular base 210 that is thicker than the base 110. The strip brush elements 170 are then slidably secured in the channels 246.

Figure 6:
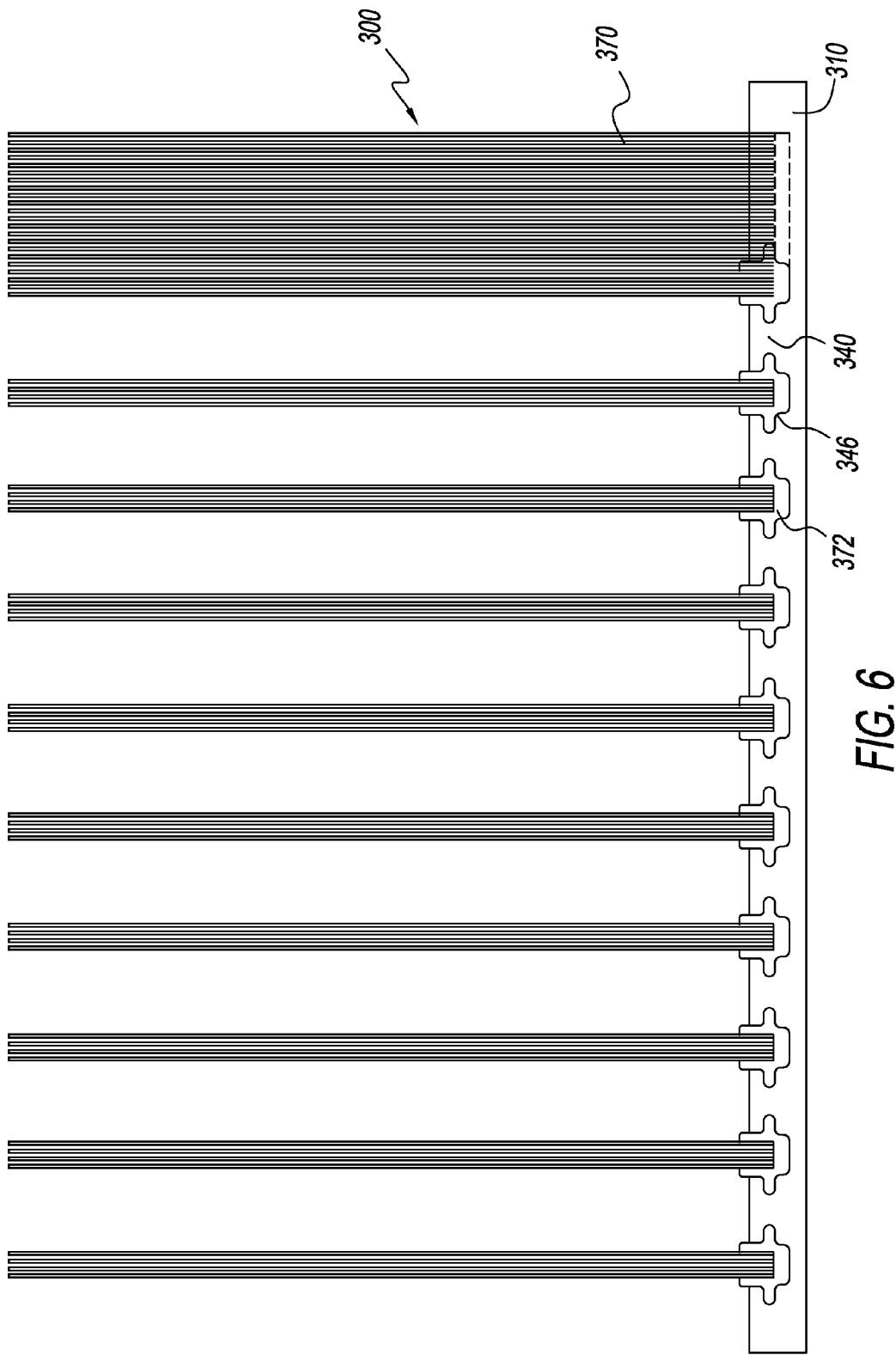
FIG. 6 is a side view of another embodiment of the brush of the present invention similar to FIG. 1 but with curved rails.
Figure 7:
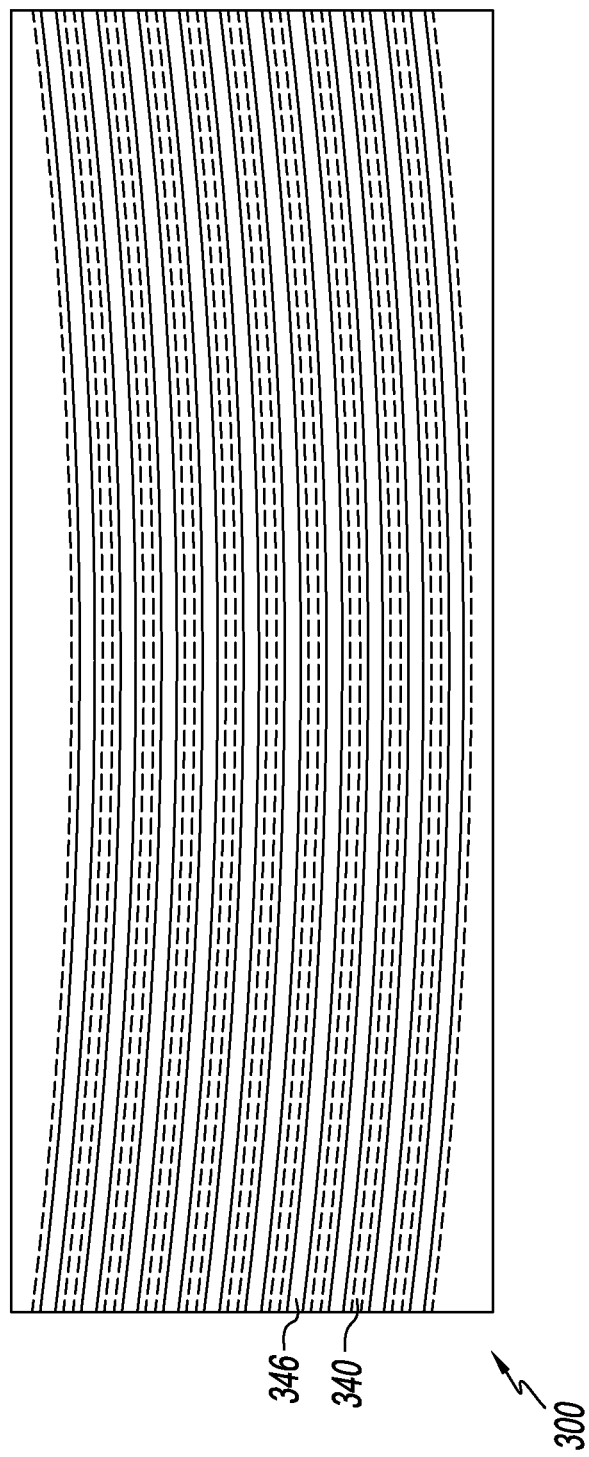
FIG. 7 is a top view of the base and rails of FIG. 6.
Figure 8A:
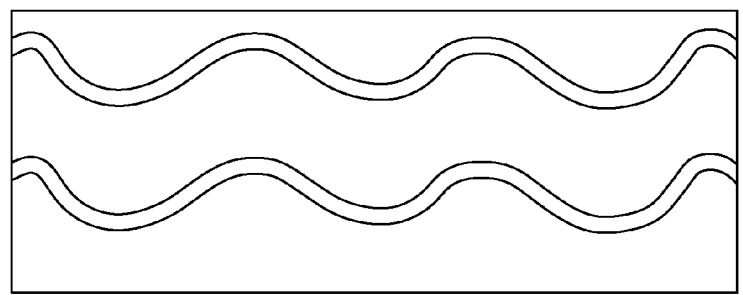
FIGS. 8A-8D illustrate different channel patterns on a planar base.
Figure 8B:
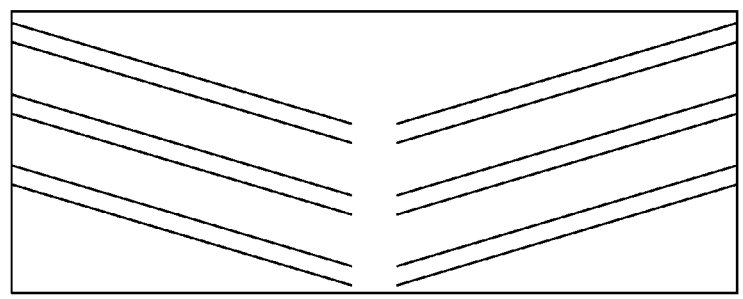
Figure 8C:
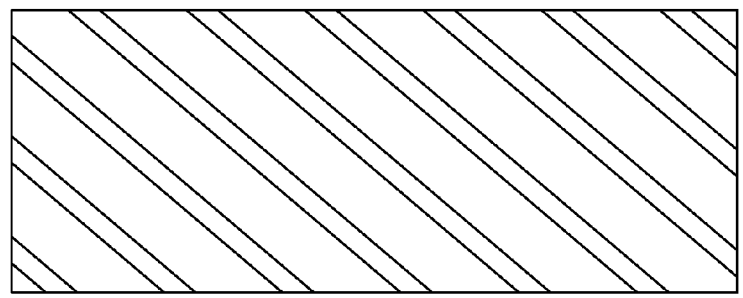
Figure 8D:

FIGS. 6 and 7 show a brush 300 similar to brush 200 of FIG. 5. The front view of the brush 300 is the same as FIG. 3. The difference between the brush 300 and brush 200 is that the integral rails 340, and the corresponding channels 346, are curved. Such curved channels 346 are difficult, if not impossible, to produce with any prior art method. While the rails 340 are shown to be integral with the base 310, the rails 340 can be fastened to the base 310 as discussed in connection with brush 100 of FIGS. 1-3. To facilitate the slidable insertion of the strip brush element 370 into the curved channels 346, the coupling end 372 of the strip brush element 370 is narrow or flexible.

Figure 9A:
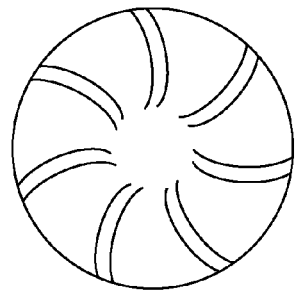
FIGS. 9A-9F illustrate different planar shape base.
Figure 9B:
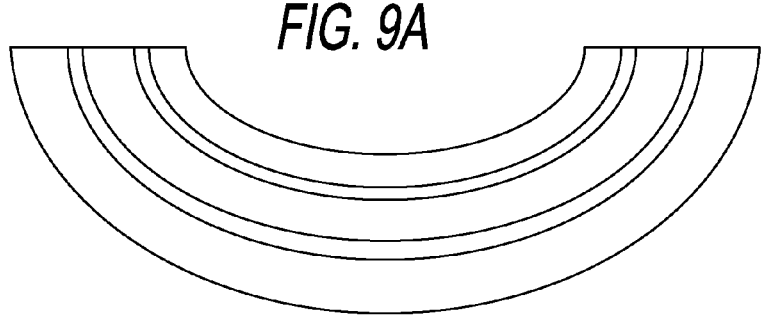
Figure 9C:
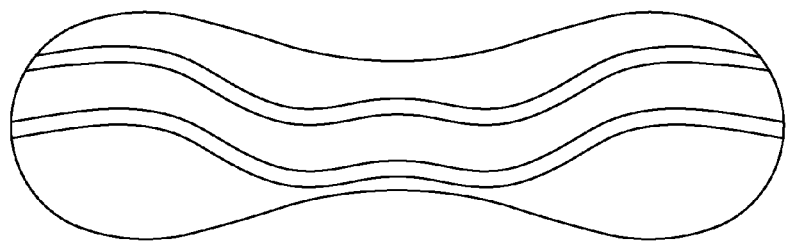
Figure 9D:
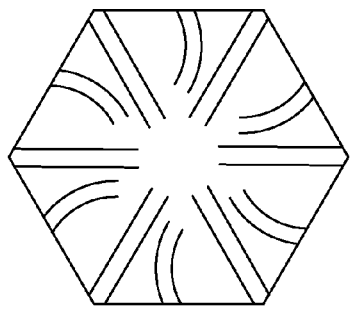
Figure 9E:
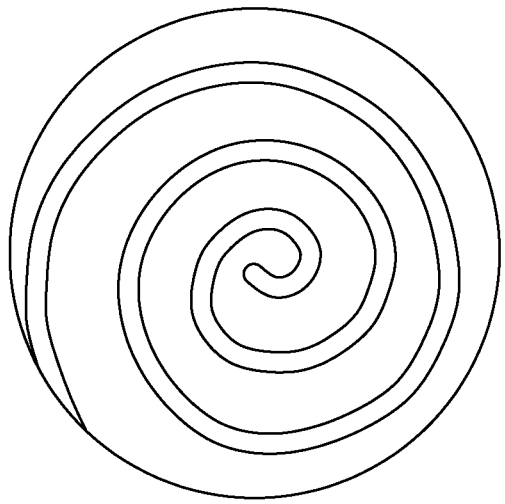
Figure 9F:
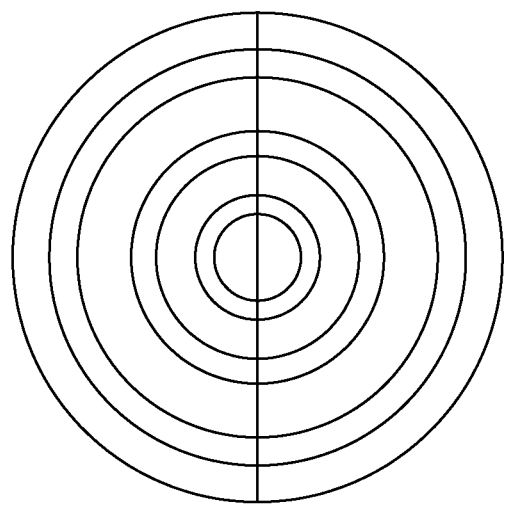

The brushes 100, 200 and 300 as shown in FIGS. 1-3 and 4-6 are ideally, but not limited to be, used as sweep-backs for use with forklifts. Brush 300 having curved rails 340 and corresponding curved channels 346 aids in the guiding of debris during sweeping. Other channel patterns, not limited to those illustrated in FIGS. 8A-8D, can be used for the brush of the present invention. The densities and widths of the channel shown in FIGS. 8A-8D can be customized. While the brushes 100, 200 and 300 of FIGS. 1-3 and 4-6 each has a planar rectangular base 110, 210 and 310, different shapes planar base, not limited to those illustrated in FIGS. 9A-9E, can also be used. The channel patterns shown in FIGS. 9A-9F are merely for illustration only and other channel patterns can be used in those bases. FIG. 9F illustrates a base formed from two identical parts that are put together after the strip brush elements 170 are inserted between adjacent rails 140.

Figure 10:
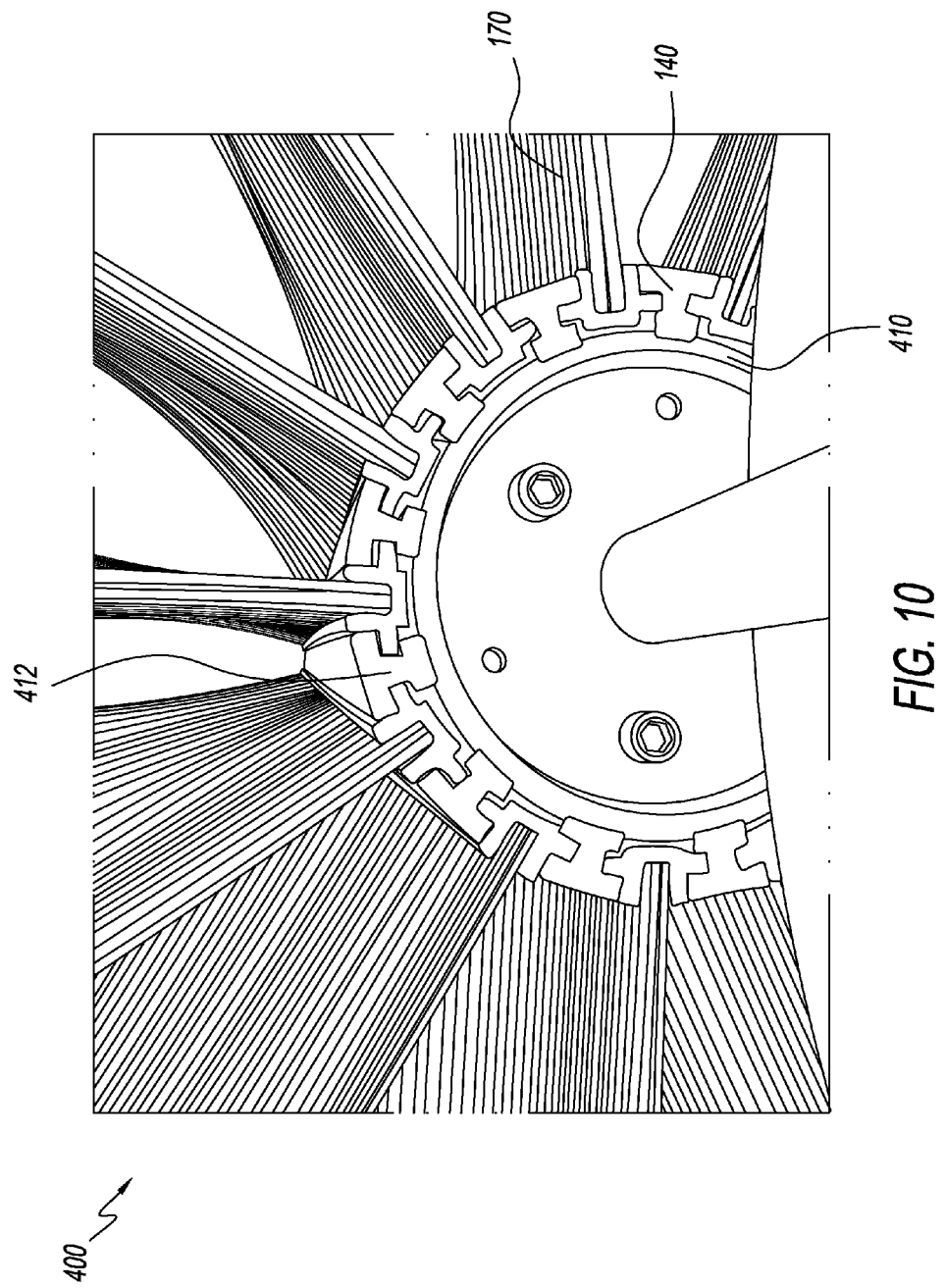
FIG. 10 is a side view of another embodiment of the brush of the present invention having a tubular base.
Figure 11:
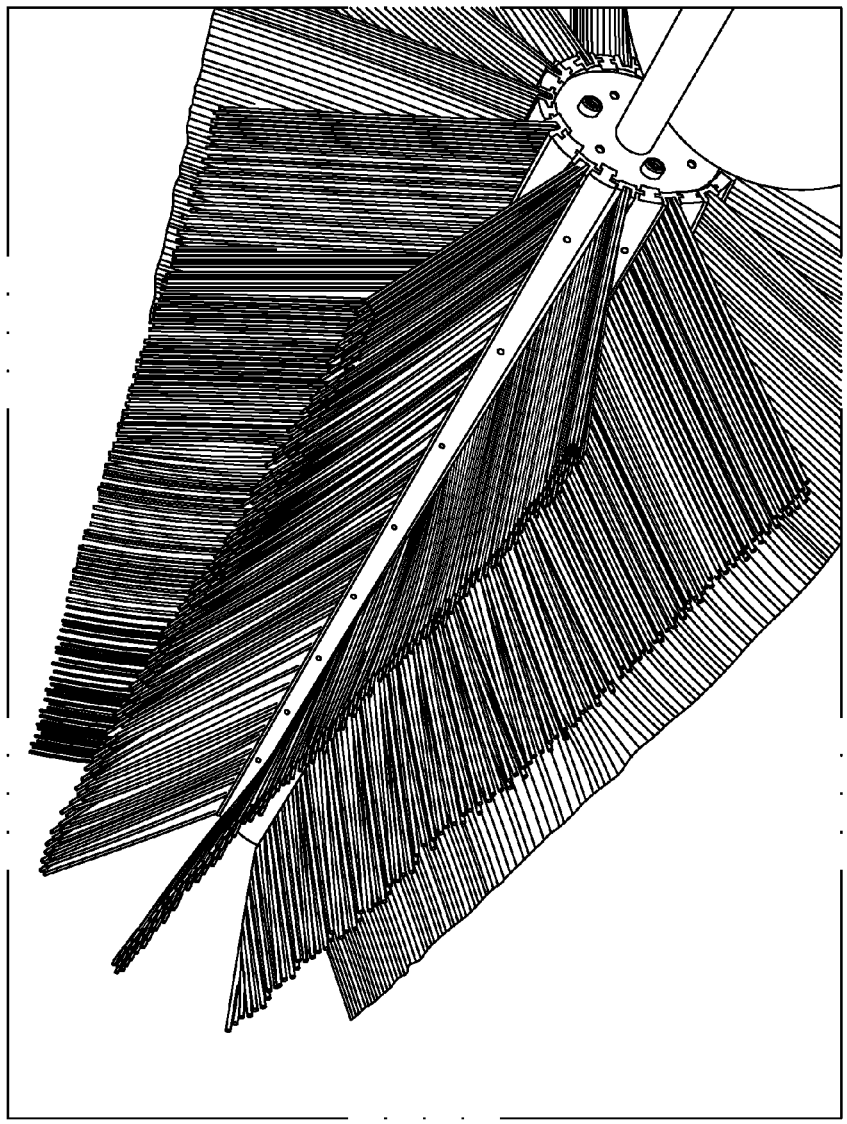
FIG. 11 is a perspective view of FIG. 10.
Figure 12A:
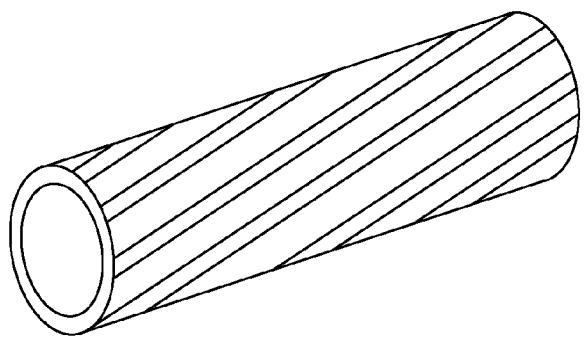
FIGS. 12A-12D illustrate different channel patterns on a tubular base.
Figure 12B:
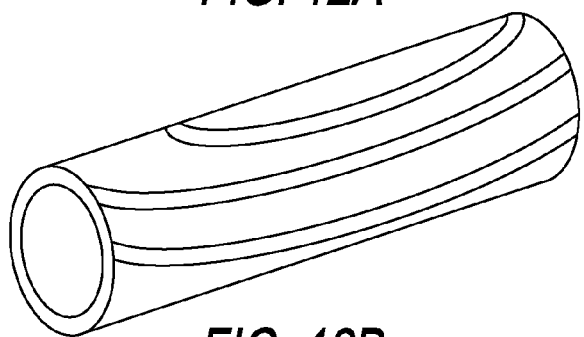
Figure 12C:
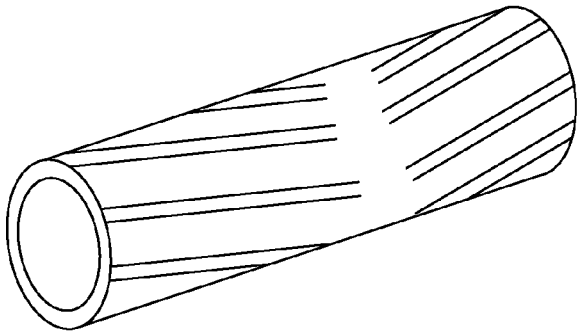
Figure 12D:
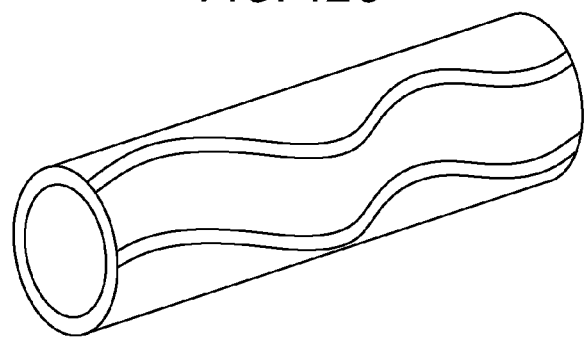

FIGS. 10-11 show a brush 400 having a tubular base 410 with a plurality of spaced apart and longitudinal grooves 412 on its surface. Similar to the brush 100, fastened to the grooves 412 are a plurality of rails 140; adjacent rails 140 define a channel 146; and a strip brush element 170 is slidably received in each channel 146. Similar to the brush 200, rails 140 can also be integrally formed from the base 410 using a thicker tubular base 410. Different channel patterns, not limited to those illustrated in FIGS. 12A-12D, can also be used on the tubular base 410.

Figure 13:
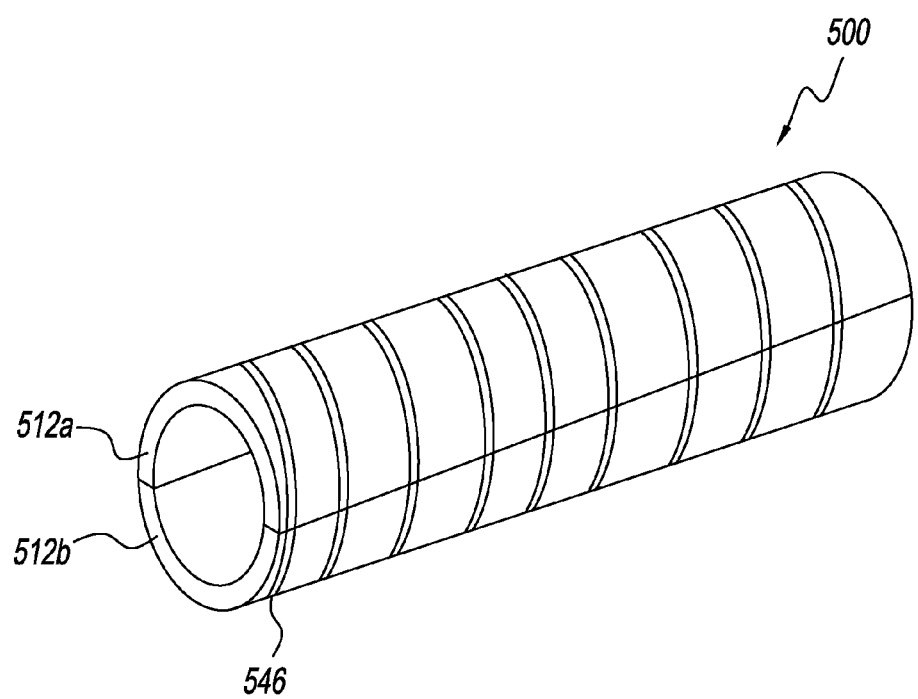
FIG. 13 is a perspective view of another embodiment of the brush of the present invention having two corresponding arcuate bases.
Figure 15A:
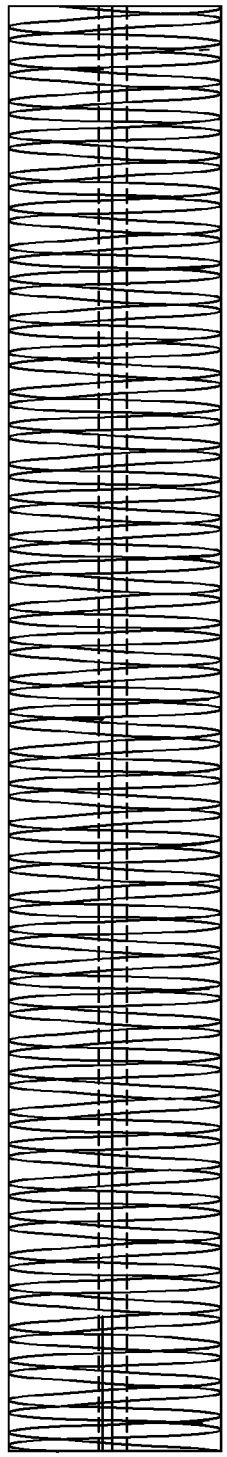
FIGS. 15A-15B illustrate different channel patterns.
Figure 15B:
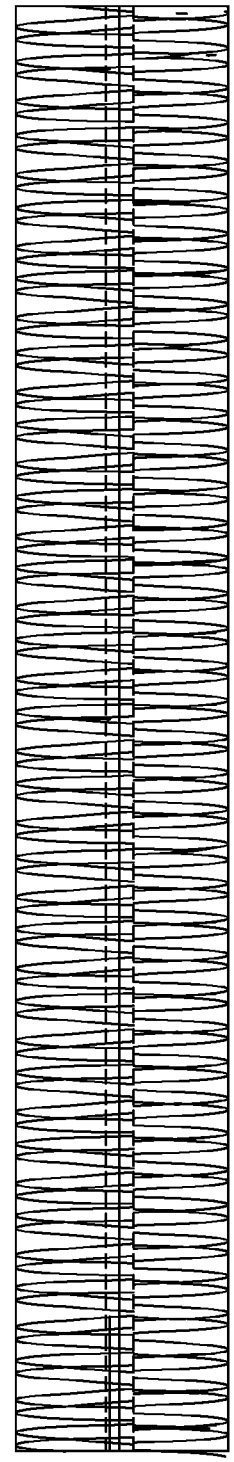

FIGS. 13 and 14 show a brush 500 having a tubular base 510 formed from two corresponding arcuate bases 512a and 512b. Fastened to each arcuate base 512 is a plurality of semi-circular rails 540 defining semi-circular channels 546 therebetween for receiving strip brush elements 170. A plurality of grooves 512 may be provided on the surface of the arcuate base 512 to receive the rails 540. To assemble brush 500 from the components, each arcuate base 512 are first fastened with semi-circular rails 540, then strip brush elements 170 are then slidably inserted into the channels 546. Once each arcuate base 512 is filled with the strip brush elements 170, the two arcuate base 512*a* and 512*b* are then interconnected to form a tubular base. The interconnection of the arcuate bases 512*a* and 512*b* is shown in FIG. 14 as a tongue and groove combination, but other methods of interconnection known to one skilled in the art can also be used. The resulting brush 500 has circular strip brush elements 170 around the circumference of the tubular base, similar to a wafer broom. The configuration of brush 500 is not achievable with the prior art processes of extrusion or welding of the channels. While brush 500 is shown to have circular strip brush elements 170, the rails 540 and corresponding channels 546 may be at an angle such that the strip brush elements 170 form an oval or elliptical shape (not shown). Further, as illustrated in FIG. 15A the channels 546 can form a continuous helical pattern or as illustrated in FIG. 15B, the channels 546 of FIG. 15A can be offset so that they do not form a continuous helical pattern.

Figure 16:
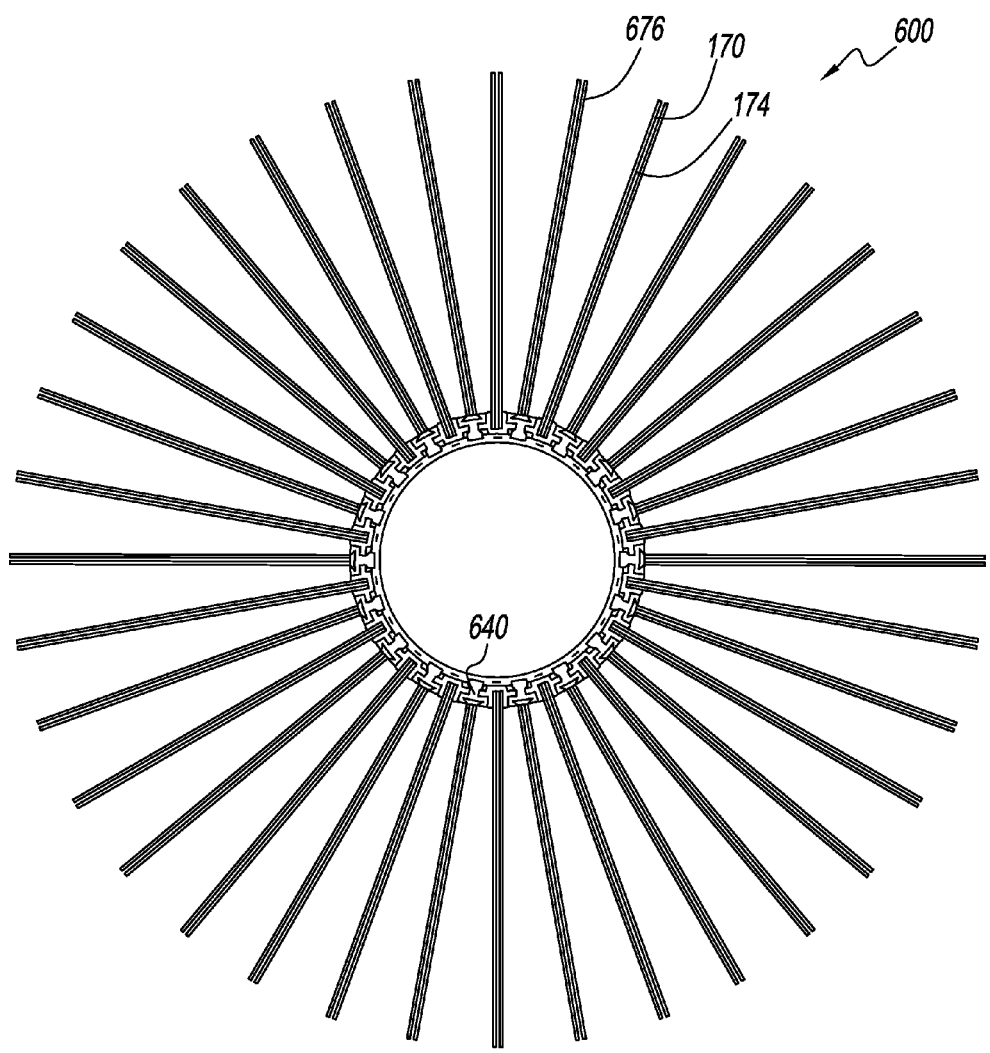
FIG. 16 is a side view of another embodiment of the brush of the present invention having a second set of brush elements.

FIG. 16 shows a brush 600 similar to brush 400 of FIGS. 10-11, except that there is a second set of brush elements 676 extending from the upper surface of each rail 640. The resulting brush 600 provides twice the density of brush elements of brush 400. The brush elements 174 of the strip brush element 170 between adjacent rails 640 and the second set of brush elements 676 may be made of the same or different materials, depending on the specific application of brush 600. Instead of having the second set of brush elements 676 extending directly from the rails 640 as shown in FIG. 16, each rail 640 can alternatively have an elongated canal (not shown) on the upper surface for receiving a strip brush element 170.

Figure 17:
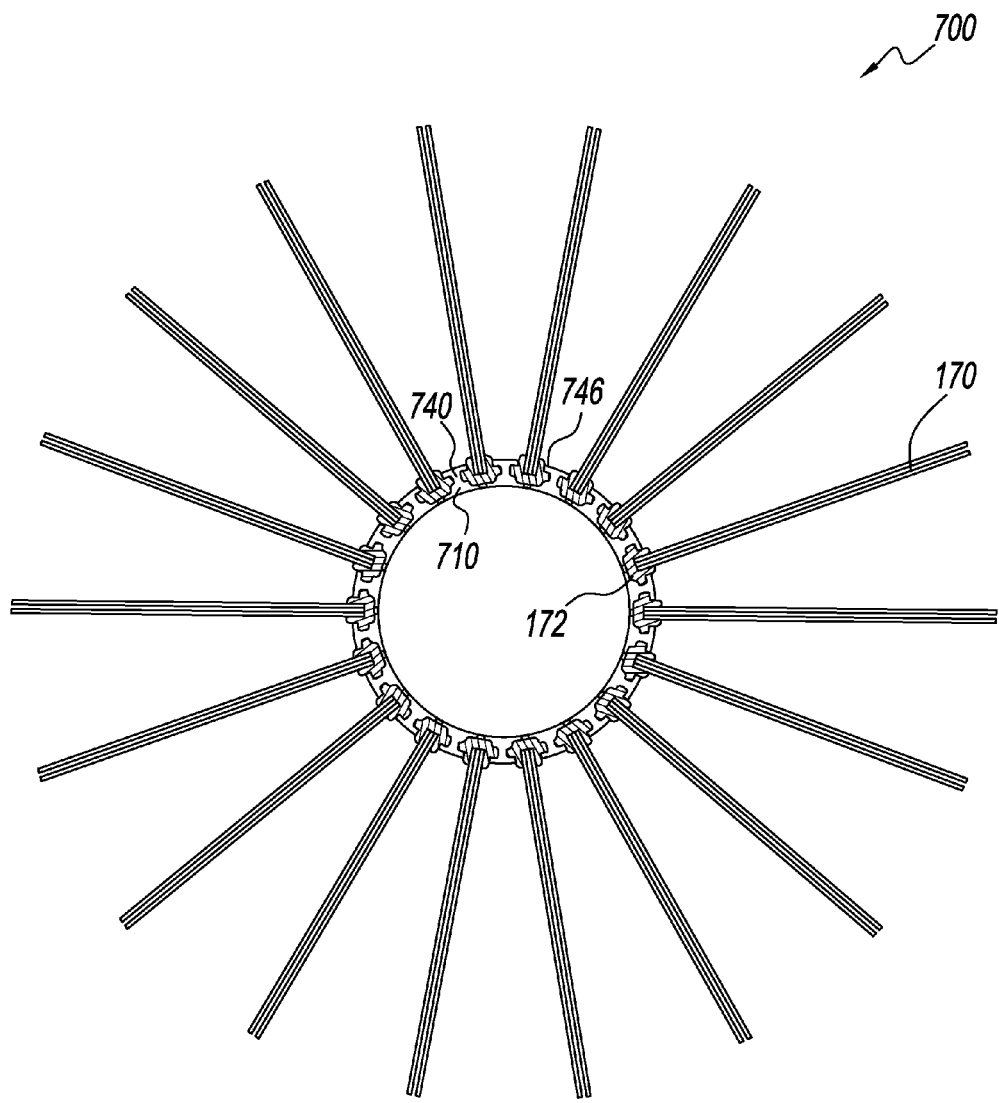
FIG. 17 is a side view of another embodiment of the brush of the present invention similar to FIG. 10 but with integral rails.
Figure 18:
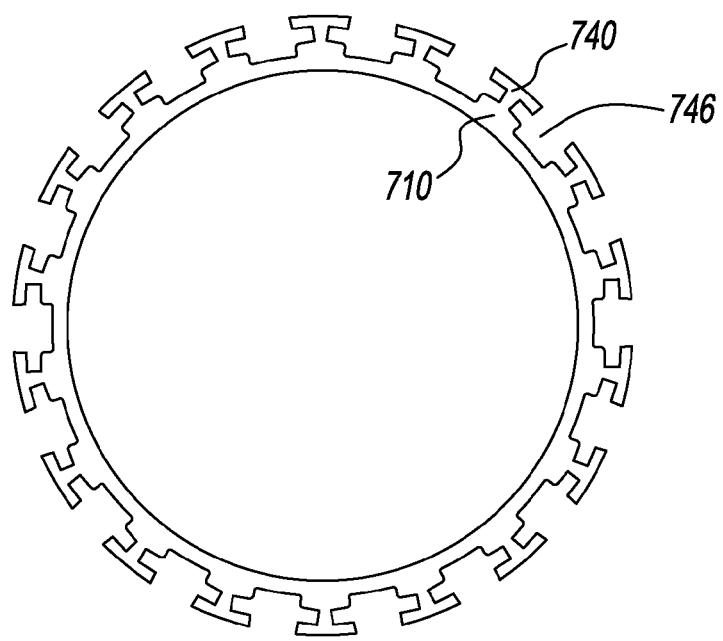
FIG. 18 is a side view of FIG. 17, without the strip brush elements.

FIGS. 17 and 18 show a brush 700 similar to brush 400 of FIGS. 10-11, except that brush 700 has integral rails 740. Rails 740 are formed integrally with tubular base 710 by cutting, carving, grounding, etching or milling a plurality of channels 746 on the surface of a tubular base 710 that is thicker than the base 410. The channels 746 can tightly conform to the shape of the coupling end 172 of a strip brush element 170 to minimum rocking of the strip brush element 170 during use.

Figure 19:
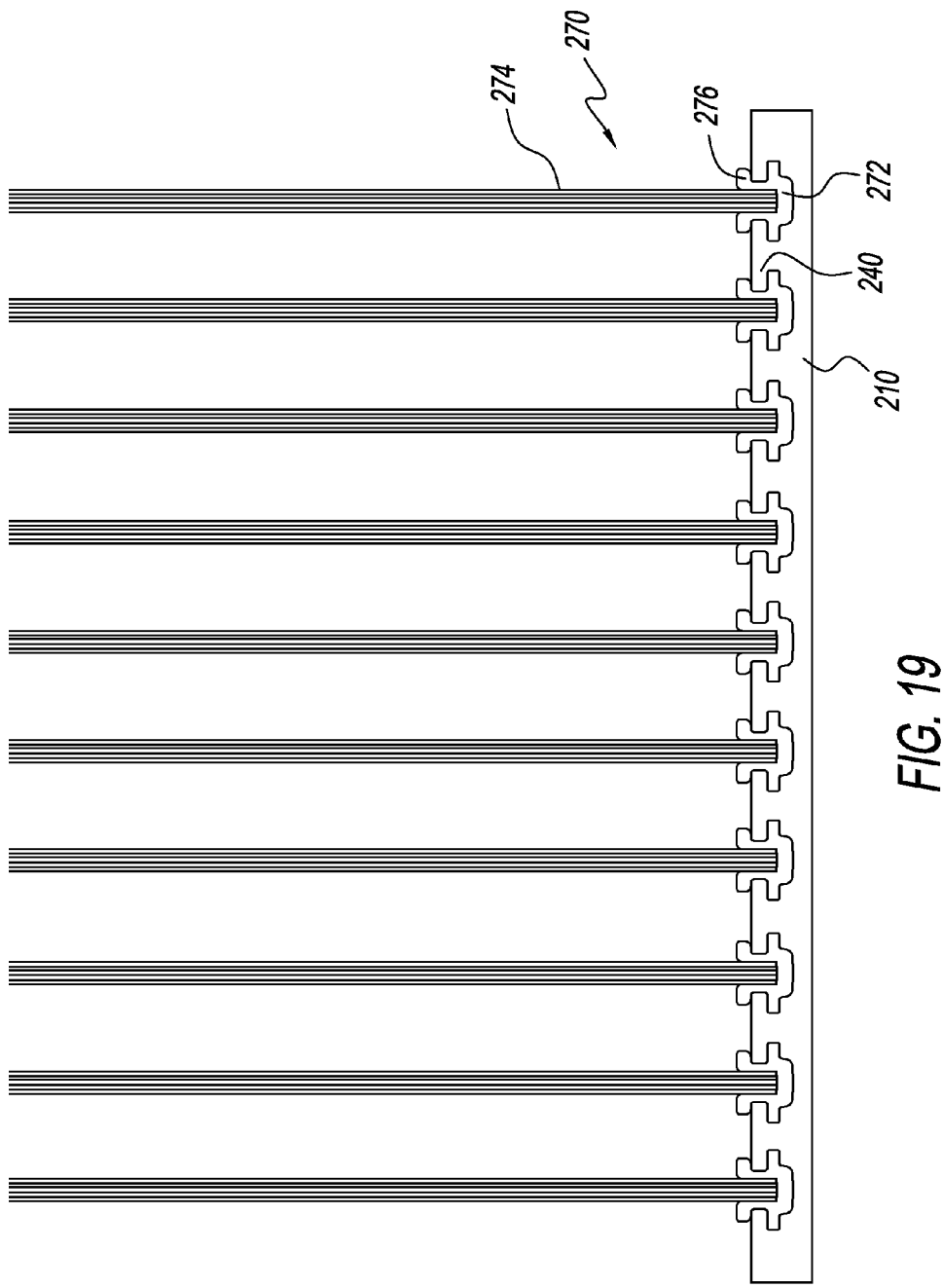
FIG. 19 is a side view of another strip brush element of the present invention.

FIG. 19 shows another embodiment of the strip brush element 270 that can be used in connection with any base and rail described herein. Similar to strip brush element 170, strip brush element 270 has a coupling end 272 and a brush element 274 extending therefrom. The upper portion of the coupling end 272 has stabilizing lip 276 that overlay the upper portion of the rail 240 to stabilize, and to minimizing rocking of, the strip brush element 270 when in use.

Figure 20:
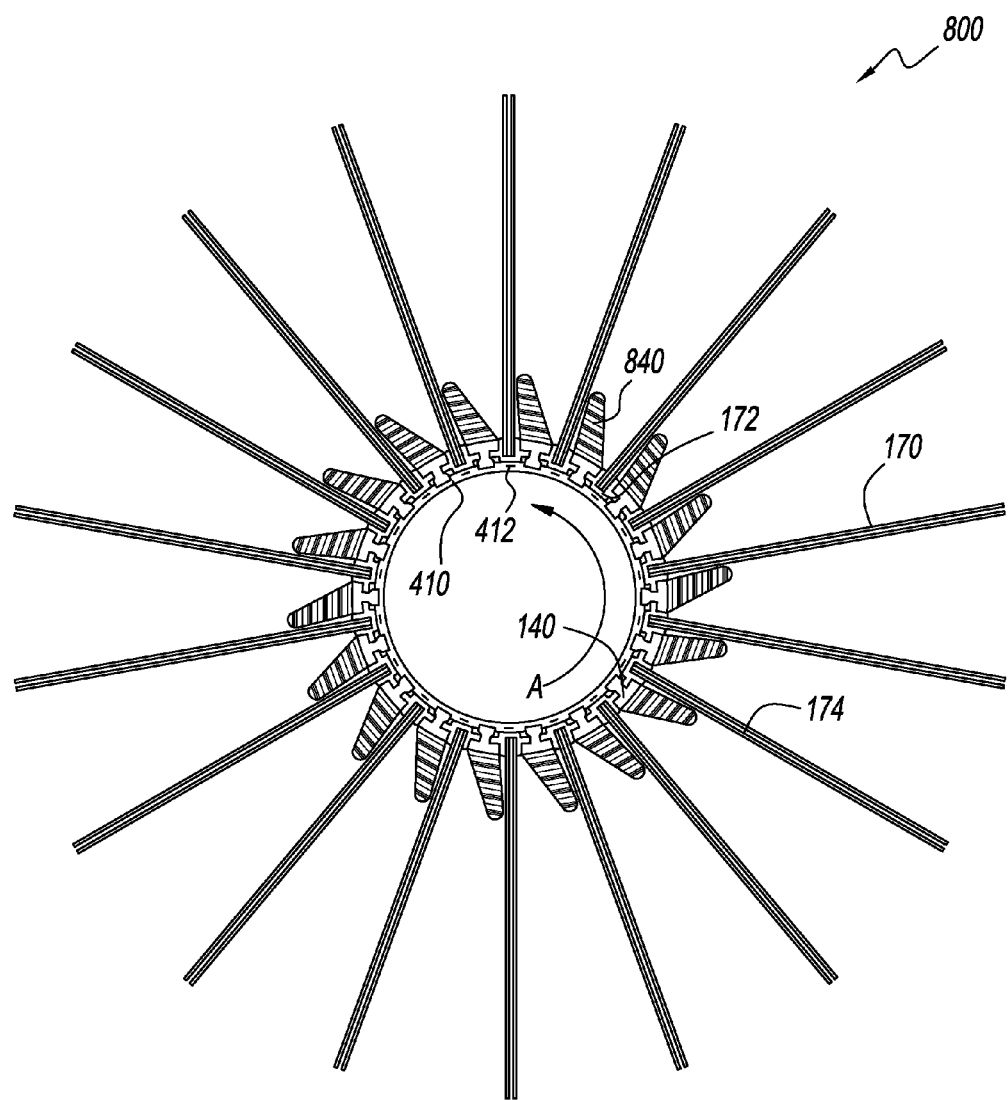
FIG. 20 is a side view of another embodiment of the brush of the present invention similar to FIG. 10 but having a support element for the bristles.

FIG. 20 shows a brush 800 similar to brush 400 of FIG. 10, except that brush 800 has a support element 840 extending radially away from the tubular base 410 from the top of the rail 140. The support element 840 has a generally triangular prism shape that extends longitudinally along and on the rail 140. The support element 840 can be made of the same material as the remaining components of the brush 800, be integrally extruded along with the rail 140 or be removably attachable to the rail 140. The unique shape of the support element 840 provides contact with the brush element 174, and thereby supports the brush element 174, at a point other than the coupling end 172 of the strip brush element 170. As a result, when brush 800 is rotated in the direction A, the brush element 174 as supported by the support element 840 changes the stress point of the brush element 174 to produce a different brush action than a brush element 174 without the support element 840 (as in brush 400 of FIG. 10). Further, brush 800 can use finer (smaller diameter) brush element 174 to result in the same strength as a wider diameter brush element 174 used in brush 400 of FIG. 10 while using less material and having the sweeping attribute of a finer brush element 174. The support element 840 may have a different shape than the generally triangular prism shape as shown as long as it provides contact and support to the brush element 174 at a point higher than the coupling end 172 of the strip brush element 170. Further, the support element 840 may not be continuous longitudinally and may be a plurality of discrete elements spaced apart along the longitudinal length of the rail 140 to provide a different brush action. Instead of being similar to brush 400 of FIG. 10, brush 800 can be similar to brush 700 of FIGS. 17 and 18, with the support element 840 integrally formed from milling the channels and support elements from a thicker base.

FIG. 21A-21B show the partial side and top views of a brush 900 similar to brush 400 of FIG. 10, with the mid section 972B of the coupling end 972 of the strip brush element 970 formed from a plurality of fingers 973 to allow one way insertion of the strip brush element 970 into the channel 146. As shown, one side of the mid section 972B of the coupling end 972 of the strip brush element 970 has a plurality of fingers 973 disposed at an angle to form a feather board. The width of the mid section 972*b* is slightly wider than the mid space 149 of channel 146 such that the strip brush element 970 is inserted into the channel 146 in one direction only (direction B). The fingers 973 compress slightly into the mid space 149 for insertion and for a snug and frictional hold in the channel 146, which prevent movement of the strip brush element 970 in the opposite direction. Mid portion 143 of the rail 140 adjacent the fingers 973 may have spaced-part bumps thereon to further prevent the movement of the strip brush element 970 in the opposition direction. While FIGS. 21A-21B show that one side of the mid section 972B has fingers 973, both sides of the mid section 972B can optionally have fingers 973. Further, instead of having the fingers 973 in the mid section 972B of the strip brush element 970, the fingers may extend from the mid portion 143 of the rails to produce the same result. The fingers 973, whether on the strip brush element 970 or rail 140, can be produced after the strip brush element 970 or rail 140 is extruded and passing it through a gear wheel, etc. to produce the fingers 973.

In the discussion of the various embodiments above, the strip brush elements 170 is slidably insertable longitudinally into the channels 146 between adjacent rails 140. The strip brush element 170 may also be snapped into the channel 146, in a side-by-side fashion, if alternating rails 140 having different rigidities are provided. For example, one rail 140 can be made out of a rigid material and the adjacent rail 140 be made out of a flexible material such that one side of the coupling end 172 of the strip brush element 170 is first inserted into the rigid rail 140 and then the other side of the coupling end 172 is forced past the flexible rail 140 for complete insertion of the coupling end 172 into the channel 146.

One of the advantages of the brush system of the present invention is the efficiency and ease in producing a customized brush. There is no need for highly skilled welding professionals, and the process of fastening the rails to the base can be easily accomplished by a non-skilled laborer. A method of fastening the rails to the base is by applying adhesive to the lower portion of the rail and then placing the rails on the surface of the base; the rails can be held in place either manually or with a clamp until the adhesive is set. Additional fasteners such as screws, rivets, nuts and bolts, can be used to ensure secure attachment. Such efficiency and ease similarly extends to the repair of the customized brush. The most common place for failure, due to fatigue or misuse, of a prior art brush is the detachment of the U-shape channels from the base. If similar failure occurs with the brush of the present invention, the rails can easily be re-fastened, e.g. by adhesive, to the base to allow the brush to function once again.

Another advantage of the brush system of the present invention is the ability to custom design a brush to create a more efficient sweeping pattern (or other desired effects such as brushing, deflecting, mopping, or acts as a spray suppressant) for various applications.

Another advantage of the brush system of the present invention is the ability to produce a brush entirely made of thermoplastic or thermoset. Further, such brush may be entirely recyclable. Such brush also lends itself to certain applications of the brush in a wet environment because there is no metal part that may rust. This is an especially important aspect for a brush being used in an underwater (fresh or salt water) environment where typically expensive stainless or aluminum prior art brush is required. The use of thermoplastic or thermoset material also facilitates the addition of different additives to the plastic to change either the material composition or to add color for identification purposes. In a prior art brush, a completely separate set up is required to paint the brush different colors.

Another advantage of the brush system of the present invention is the ability to customize a base with rails that is reusable with the replacement of the strip brush elements as they are worn out from use. Further, the customized base with rails can replicate all existing brushes in all industries and applications. Still further, the base with rails can advantageously be customized to accept or receive existing strip brush elements.

The features of the invention illustrated and described herein are the preferred embodiments. Therefore, it is understood that the appended claims are intended to cover the variations disclosed and unforeseeable embodiments with insubstantial differences that are within the spirit of the claims.

What I claim is:

1. A method of producing a brush from modular components, comprising the steps of:
    providing a unitary base having a surface;
    milling at least one elongated channel at a selective location on said surface, each said channel having a cross section with a narrower upper space and a wider lower space;
    providing at least one elongated strip brush element having a coupling end and a first set of brush element extending from said coupling end, said coupling end having a cross section with a narrower upper section and a wider lower section corresponding to said narrower upper space and wider lower space, respectively, of said channel; and
    slidably inserting said coupling end of said strip brush element in said channel to be removably held therein.

2. The method of claim 1 wherein said channels are linear.

3. The method of claim 1 wherein said channels are non-linear.

4. The method of claim 1 further comprising the step of providing means for holding said strip brush element in said channel.

5. The method of claim 1 wherein said surface of said base is planar.

6. The method of claim 1 wherein said surface of said base is non-planar.

7. The method of claim 1 providing a plurality of channels and a plurality of strip brush elements, further comprising the step of forming a predetermined pattern on said surface of said base from said plurality of channels and said plurality of strip brush elements.

8. The method of claim 1 wherein said base and strip brush elements are made of a thermoplastic material.

9. The method of claim 1 wherein said base and strip brush elements are made of a thermoset material.

10. The method of claim 1, wherein said base and strip brush elements are made of a non-corrosive material.

11. The method of claim 1 wherein said base is formed from two corresponding parts.

12. The method of claim 1 providing a plurality of channels, further comprising the step of providing a second set of brush element extending from said surface of said base between adjacent channels.

13. The method of claim 1 further comprising the step of providing a stabilizing lip extending from said upper section of said coupling end such that said stabilizing lip overlay said surface of said base.

14. The method of claim 1 further comprising the step of providing a plurality of fingers at said coupling end such that said coupling end is slidably insertable into said channel in one direction only.

15. The method of claim 1 further comprising the step of milling at least one support element between adjacent channels such that said support element is in contact with said first set of brush element.

16. A brush prepared by a process comprising the steps of:
    providing a unitary base having a surface;
    milling at least one elongated channel at a selective location on said surface, each said channel having a cross section with a narrower upper space and a wider lower space;
    providing at least one elongated strip brush element having a coupling end and a first set of brush element extending from said coupling end, said coupling end having a cross section with a narrower upper section and a wider lower section corresponding to said narrower upper space and wider lower space, respectively, of said channel; and
    slidably inserting said coupling end of said strip brush element in said channel to be removably held therein.

17. A modular brush system, comprising:
    a unitary base having a surface;
    at least two adjacent elongated rails selectively fastened to said surface of said base defining a channel between said adjacent rails, each said rail having a cross section with a wider upper portion and a narrower lower portion, and said channel having a cross section with a narrower upper space and a wider lower space; and
    at least one elongated strip brush element having a coupling end and a first set of brush element extending from said coupling end, said coupling end having a cross section with a narrower upper section and a wider lower section corresponding to said narrower upper space and wider lower space, respectively, of said channel to be removably held within said channel abutting said surface;
    wherein said base, said rails and said elongated strip brush elements are made of a plastic material.

18. The modular brush system of 17, wherein said base, rails and elongated strip brush elements are made of a thermoplastic material.

19. The modular brush system of 18, wherein some of said base, rails and elongated strip brush elements are made of a rigid thermoplastic material.

20. The modular brush system of 17, wherein said base, rails and elongated strip brush elements are made of a thermoset material.

21. The modular brush system of 20, wherein some of said base, rails and elongated strip brush elements are made of a rigid thermoset material.

* * * * *